United States Patent
Cellier et al.

(10) Patent No.: US 8,871,465 B2
(45) Date of Patent: Oct. 28, 2014

(54) **METHOD FOR IDENTIFYING BACTERIA FROM THE *BACILLUS CEREUS* GROUP**

(75) Inventors: Marie Cellier, Montalieu Vercieu (FR); John Mills, Fenton, MO (US); David Mosticone, Sainte Consorce (FR); Sylvain Orenga, Neuville sur Ain (FR); Antoine Vimont, Lyons (FR)

(73) Assignee: bioMérieux, S.A., Marcy L'Etoile ( * ) Notice: Subject to any disclaimer, the term of this patent is extended or adjusted under 35 U.S.C. 154(b) by 0 days.

(21) Appl. No.: 13/496,422

(22) PCT Filed: Sep. 16, 2010

(86) PCT No.: PCT/FR2010/051925
§ 371 (c)(1),
(2), (4) Date: Mar. 15, 2012

(87) PCT Pub. No.: WO2011/033224
PCT Pub. Date: Mar. 24, 2011

(65) Prior Publication Data
US 2012/0171709 A1  Jul. 5, 2012

(30) Foreign Application Priority Data
Sep. 18, 2009 (FR) .................. 09 04470

(51) Int. Cl.
*C12Q 1/04* (2006.01)
(52) U.S. Cl.
USPC .................. 435/34; 435/253.6
(58) Field of Classification Search
USPC .................. 435/34, 253.6
See application file for complete search history.

(56) References Cited

U.S. PATENT DOCUMENTS

| | | | |
|---|---|---|---|
| 6,284,517 B1 | 9/2001 | Restaino | |
| 6,558,917 B2 * | 5/2003 | Schabert | 435/34 |
| 7,309,580 B2 * | 12/2007 | Restaino | 435/34 |
| 2004/0005652 A1 | 1/2004 | Restaino | |
| 2011/0129871 A1* | 6/2011 | Mosticone et al. | 435/36 |

FOREIGN PATENT DOCUMENTS

EP   1219628   7/2002

OTHER PUBLICATIONS

Durban M. et al. An Assay System for the Detection of Phospholipase C Activity. Eur J Lipid Sci 105(1)633-637, Oct. 2003.*
Juergensmeyer M. et al. A Selective Chromogenic Agar . . . J of Food Protection 69(8)2002-2006, 2006.*
Peng H. et al. Isolation and Enumeration of *B. cereus* from Foods on a Novel Chromogenic Plating Medium. Food Microbiology 18:231-238, 2001.*
The English Translation of International Search Report dtd Mar. 24, 2011 for PCT/FR2010/051925.
The English Translation of Written Opinion dtd Apr. 4, 2012 for PCT/FR2010/051925.
Jürgensmeyer et al, Journal of Food Protection, 2006, pp. 2002-2006, vol. 69, n° 8.
Fricker et al, Intern. Journal of food microbiology, 2008, pp. 27-34, vol. 121, n° 1.
Manafi et al, Microbiological Review, 1991, pp. 335-348, vol. 55, n° 3.

* cited by examiner

*Primary Examiner* — Ralph Gitomer

(57) ABSTRACT

The present invention relates to a method for identifying bacteria of the *Bacillus cereus* group, comprising the following steps: (a) providing a sample that may contain bacteria of the *Bacillus cereus* group, a reaction medium comprising at least one fluorescent phosphatidylcholine phospholipase C (PC-PLC) substrate and an inhibitor of Gram-negative bacteria; (b) inoculating the reaction medium with the sample; (c) incubating the inoculated reaction medium; and (d) identifying the bacteria of the *Bacillus cereus* group by detecting the PC-PLC substrate hydrolysis reaction, in which the pH of the reaction medium and the time necessary for detecting the PC-PLC substrate hydrolysis reaction are adapted such that said hydrolysis reaction by bacteria of the *Bacillus cereus* group is detected before hydrolysis of the PC-PLC substrate by any Gram-positive bacteria other than those belonging to the *Bacillus cereus* group, that may be present in the sample.

10 Claims, 2 Drawing Sheets

METHOD FOR IDENTIFYING BACTERIA FROM THE *BACILLUS CEREUS* GROUP

CROSS REFERENCE TO RELATED APPLICATIONS

This application is the national stage application under 35 U.S.C. §371 of International Application No. PCT/FR2010/051925, filed Sep. 16, 2010, which claims the benefit of French Patent Application No. 0904470, filed Sep. 18, 2009, the disclosures of which are hereby incorporated by reference.

The present invention relates to the field of microbiological testing of food. More particularly, it relates to a method for distinguishing between bacteria of the *Bacillus cereus* group and other bacteria, by hydrolysis of a fluorescent substrate for lecithinase or phosphatidylcholine phospholipase C, hereinafter referred to as PC-PLC.

Microbiological testing in the food-processing field requires the implementation of techniques which allow the detection and/or identification and/or counting of microorganisms, and the results of which must be provided as rapidly as possible. Said microorganisms may be nonpathogenic, such as bacteria of technological interest, for instance ferments, or such as quality indicators; the latter make it possible to validate the production process, from the raw materials or crude products, to the final products. Nevertheless, said microorganisms are most commonly pathogenic, and the rapid and accurate detection of presumed contaminations makes it possible to take corrective steps. Alternatively, the toxins produced by said microorganisms and responsible for pathogenic effects may be investigated.

Clinical diagnosis uses the same techniques: either the detection and/or counting of the bacteria themselves, or the detection of the toxins. In any event, the important factors for diagnostic tests are: sensitivity, selectivity and time for the result to be obtained.

The *Bacillus* genus comprises Gram-positive bacteria present ubiquitously in nature: in the ground, the water, the air, and also in food products, from cereal grains to powdered milks, floury products, spices. The ability to form spores gives them a very great resistance in the external environment. The spores of *Bacillus cereus* (*B. cereus*), in particular, can soil foods, from the raw materials to the manufactured products. Said spores survive throughout the length of the food chain. Under normal circumstances, *B. cereus* is present in an amount of less than $10^3$ cells per gram of food and has no pathogenic effect. The minimum pathogenic level is greater than $10^5$ cells per gram of food. The contamination of an individual from a food can thus be responsible for gastroenteritis. Gastroenteritis associated with *B. cereus* is effected either by vomiting or by diarrhea. Various foods may be incriminated: meats, rice, dehydrated meals, sauces, soups, etc. Opportunistic infections with *B. cereus* can also be observed in weakened patients, such as alcoholic or immunodepressed individuals or following injuries such as burns.

The detection and quantification of bacteria of the *Bacillus cereus* group is therefore essential for the testing laboratories of the food-processing industry and for clinical diagnosis laboratories. In a standard manner, the isolation is carried out on conventional selective plating culture media: for example, standards of ISO (International Organization for Standardization) type or BAM-FDA (Bacteriological Analytical Manual of the Food and Drug Administration) methods recommend media such as polymyxin egg yolk mannitol bromothymol blue agar (PEMBA) or mannitol-egg yolk-polymyxin agar (MYP). The identification is carried out according to morpholigcal characteristics and culture or metabolic characteristics.

These PEMBA or MYP media can lead to potential false positives linked to an inhibitor system that is not very effective, or to false negatives linked to the possible absence of the key morphological and metabolic characteristics in certain strains. Finally, some strains exhibit ambiguous reactions, as described by Fricker et al., International Journal of Food Microbiology; 121 (2008): 27-34. Chromogenic plating media have been developed in order to overcome false negatives: they contain chromogenic natural substrates or chromogenic synthetic substrates. Enzymatic activities specific for certain bacterial strains are thus detected by cleavage of these substrates. The specificity of the detection can be improved by adding, to the culture medium, inhibiting systems, cocktails of antimicrobial and/or antifungal agents, intended to limit the growth of other microorganisms. However, the inhibitor cocktails also delay the growth of the target microorganisms, since they are intended to limit the growth of microorganisms of the same genus as said target microorganisms.

Chromogenic or fluorescent media, based on the detection of phosphatidylinositol-specific phospholipase C (hereinafter referred to as PI-PLC) activity, have been described in patents U.S. Pat. No. 6,284,517 B, EP 1 219 628 B and U.S. Pat. No. 6,558,917 B, and also in the publication by Fricker et al., 2008 (above). These media have the drawback of leading to false negatives, in particular with certain strains of the *Bacillus cereus* group not exhibiting PI-PLC activity (*B. cereus, B. mycoides, B. weihenstephanensis*) or exhibiting weak PI-PLC activity (*B. anthracis*), or to false positives. In addition, the fluorescent substrate 4MU-MIP (4-methylumbelliferyl myoinositol-1-phosphate) exhibits a reduced stability in an aqueous medium which makes draconian conditions for use obligatory, in particular a discontinuous measurement of the fluorescence, under precise pH conditions, as indicated in patent U.S. Pat. No. 6,558,917. More precisely, it is necessary to perform the culturing at acidic pH and then to basify the medium in order to increase the fluorescence, which is read at the end point. Patent U.S. Pat. No. 7,309,580 B2 describes a plating medium combining a chromogenic substrate for PC-PLC and a chromogenic substrate for PI-PLC. The respective colors, of the medium, of the first substrate and of the second substrate are different and may also be distinguished from the third color resulting from possible mixing of the enzymatic reaction products.

The BCM medium supplied by Biosynth® AG (Switzerland) uses a chromogenic substrate for PI-PLC and a system for inhibiting the non-targeted bacterial flora comprising polymyxin B, trimethoprim, sulfamethoxazole and cycloheximide. The performance levels of the test are improved compared with the standard media, but some atypical strains can remain poorly identified (Fricker et al., 2008, above).

Chromogenic media based on the hydrolysis of β-glucosidase substrates exist, such as Brilliance™ *Bacillus cereus* agar supplied by Oxoid™. However, said substrate generates Gram-positive false positives despite the presence of an anti-Gram-positive inhibiting system comprising polymyxin B and trimethoprim, and also false negatives (Fricker et al., 2008).

Finally, a chromogenic plating medium, based on the hydrolysis of a chromogenic substrate for PC-PLC, exists: R&F® *Anthracis* chromogenic agar. Said substrate provides a negative result indication for *Bacillus anthracis* in 24 hours and a potentially positive result in 48 hours. The time for obtaining the result remains long and the specificity requires the presence of several antibiotics.

It emerges from this review that, at the current time, there is no method for detecting and/or counting bacteria of the Bacillus cereus group using a reaction medium comprising an inhibitor of Gram-negative bacteria and a fluorescent substrate for PC-PLC, said reaction medium making it possible to obtain a result in 6 to 30 hours. Such a method has a real added value for clinical or industrial diagnosis, in particular in the food-processing industry.

In view of the drawbacks noted in the prior art considered above, the essential objectives of the present invention are:
- to obtain a positive result more rapidly than the existing tests;
- to reduce the number of false positives;
- to improve the sensitivity, in particular for low levels of contamination of the sample, through the use of a reduced inhibiting system;
- to provide very easy reading and interpretation through the use of a single specific substrate, it being possible for said reading to also be automated;
- to provide simplified reaction and/or culture conditions, in particular for the preparation of the medium and the stability of the substrate.

According to a first embodiment, the invention relates to a method for identifying bacteria of the Bacillus cereus group, comprising the steps consisting in:
- bringing a sample that may contain bacteria of the Bacillus cereus group, a reaction medium comprising at least one fluorescent PC-PLC substrate and an inhibitor of Gram-negative bacteria into contact, in a container;
- incubating all the above together;
- identifying the bacteria of the Bacillus cereus group by detecting the PC-PLC substrate hydrolysis reaction, in which the pH of the reaction medium and the time necessary for detecting the PC-PLC substrate hydrolysis reaction carried out are adapted in such a way that the said hydrolysis reaction by the bacteria of the Bacillus cereus group is detected before the hydrolysis of the PC-PLC substrate by the Gram-positive bacteria other than those belonging to the Bacillus cereus group, and potentially present in the sample, is detectable.

The expression "time necessary for detecting the substrate hydrolysis" is intended to mean the time which elapses between bringing the sample, the reaction medium and the substrate into contact in a container, and detecting the signal. Concretely, this time is fixed and can be likened to the reaction time. Said signal can therefore be considered to be a result. The expression "before the hydrolysis of the PC-PLC substrate by the Gram-positive bacteria other than those belonging to the Bacillus cereus group, and potentially present in the sample, is detectable" is intended to mean: before reaching, in the absence of bacteria of the Bacillus cereus group, a signal corresponding to the threshold of detection of said bacteria of the Bacillus cereus group. The result is considered to be negative if the signal obtained is not significantly different from the background noise; in other words, if it does not exceed the detection threshold. Said result is positive if the signal obtained is significantly different from the background noise.

Preferentially, the pH of the reaction medium is between 6.8 and 8.0.

Preferentially, the time necessary for detecting the PC-PLC substrate hydrolysis is between 6 and 30 hours.

The reaction medium used in the method according to the invention is preferentially in solid, liquid or gel form.

Advantageously, the reaction medium used in the method according to the invention may be a culture medium.

Advantageously, counting of the bacteria of the Bacillus cereus group that are present in the sample is also possible.

According to one particular embodiment, the method according to the invention can be carried out in microplates, microwells, microtubes, capillaries or multiwell cards such as the VITEK® or TEMPO® cards developed and marketed by the Applicant. Advantageously, the method according to the invention may be combined with an automatic microbiological testing device of TEMPO® type as developed and marketed by the Applicant.

According to another embodiment, the method according to the invention also comprises a prior pre-enrichment step.

Advantageously, the reaction medium used in the method according to the invention also comprises at least one second substrate, which is chromogenic or fluorescent. According to one particular embodiment, said substrate is a PI-PLC substrate, which makes it possible to distinguish Bacillus anthracis from Bacillus cereus and Bacillus thuringiensis.

Preferentially, the fluorescent PC-PLC substrate corresponds to 4 MU-CP (4-methyl-umbelliferyl choline phosphate).

According to one particular embodiment of the method according to the invention, the bacteria of the Bacillus cereus group are chosen from Bacillus cereus, Bacillus anthracis, Bacillus thuringiensis, Bacillus mycoides, Bacillus pseudomycoides and Bacillus weihenstephanensis, and the other bacteria are chosen from Listeria monocytogenes, Listeria ivanovii, Staphylococcus or the other species of the genus Bacillus spp., such as Bacillus subtilis, Bacillus sphaericus, Bacillus circulans, Bacillus lentus, Bacillus pumilus, Bacillus megaterium or Paenibacillus polymyxa.

The method which is the subject of the invention can be carried out by means of a kit comprising: a reaction medium containing at least one inhibitor of Gram-negative bacteria and a fluorescent substrate specific for PC-PLC. Said medium is resuspended with an aliquot of the sample to be analyzed. Advantageously, the kit for carrying out the method according to the invention can also contain a solid container of microplate, microtube, microwell, capillary or multiwell card type, such as VITEK® card or TEMPO® card, type. Preferentially, the fluorescent PC-PLC substrate used in the kit corresponds to 4-methylumbelliferyl choline phosphate (4 MU-CP). Advantageously, the kit for carrying out the method according to the invention also comprises at least one additional substrate, which is chromogenic or fluorescent. Preferentially, said substrate is a PI-PLC substrate which makes it possible to distinguish Bacillus anthracis from Bacillus cereus, Bacillus thuringiensis, Bacillus weihenstephanensis, Bacillus mycoides and Bacillus pseudomycoides.

The specificity of a test is defined by the combination of the sensitivity and the selectivity. The sensitivity is defined as the power to reveal the species being sought, when said species is present in a small amount in a test sample. A low sensitivity will be reflected by false-negative results. The selectivity is defined as the power to detect the species being sought in the sample also containing other species. The use of specific substrates for the metabolism of the species being sought improves the selectivity. However, strains which express little enzymatic activity being sought may not be detected and may lead to false-negative results. Similarly, the use of inhibitor cocktails, in other words of compounds capable of slowing down, limiting or blocking the growth of species potentially present, but the detection of which is not desired, improves the selectivity. An inhibitor system that is not very effective can lead to false-positive results.

The term "sample" is intended to mean a small part or a small amount isolated from an entity for analysis. The sample may be of industrial origin, that is to say, according to a nonexhaustive list, an air specimen, a water specimen, a specimen taken from a surface, a part or a manufactured product, or a product of food origin. Among the samples of food origin, mention may, in a nonexhaustive manner, be made of a sample of milk products (yogurts, cheeses, etc.), of meat, of fish, of eggs, of fruit, of vegetables, of water or of a beverage (milk, fruit juice, soda, etc). These samples of food origin may also come from prepared dishes or sauces. Finally, a food sample may be derived from an animal feed, such as in particular animal meals. The sample may be of biological origin, i.e. animal, vegetable or human origin. It may then correspond to a specimen taken from a biological fluid (whole blood, serum, plasma, urine, cerebrospinal fluid, organic secretion), a tissue specimen or isolated cells. This specimen can be used as it is or, prior to analysis, undergo a preparation of enrichment, extraction, concentration or purification type, according to methods known to those skilled in the art.

Microbiological testing corresponds to the analysis of a sample with the aim of isolating and/or identifying and/or counting microorganisms potentially present, such as bacteria or yeasts. The term "reaction medium" is intended to mean a medium comprising all the components necessary for the survival and/or growth of the microorganisms. This reaction medium may either serve only as a revealing medium, or serve as a culture and revealing medium. In the first case, the microorganisms can be cultured before inoculation, and, in the second case, the reaction medium also constitutes the culture medium. The reaction medium may be solid, semi-solid or liquid. The term "solid" is intended to mean, for example, a gelled medium. Preferentially, the medium according to the invention is a gelled medium. Agar is the conventional gelling agent in microbiology for culturing microorganisms, but it is possible to use other gelling agents such as, for example, gelrite, gelatin or agarose. The reaction medium according to the invention may contain optional additives such as, for example: peptones, one or more growth factors, carbohydrates, one or more selective agents, buffers, one or more gelling agents, etc. This reaction medium may be in liquid form or gel form that is ready to use, i.e. ready for inoculation in a tube or flask or on a Petri dish.

Generally, the reaction medium may in addition contain a substrate for detecting an enzymatic or metabolic activity of the target microorganisms by means of a directly or indirectly detectable signal. For direct detection, this substrate can be linked to a part which acts as a label, which may be fluorescent or chromogenic. For indirect detection, the reaction medium according to the invention may in addition comprise a pH indicator, sensitive to the variation in pH induced by the consumption of the substrate and revealing the growth of the target microorganisms. Said pH indicator may be a chromophore or a fluorophore. As examples of chromophores, mention will be made of neutral red, aniline blue and bromocresol blue. The fluorophores comprise, for example, 4-methylumbelliferone, hydroxycoumarin derivatives or resorufin derivatives. Thus, the fluorescent PC-PLC substrate preferentially used for carrying out the method according to the invention corresponds to 4-methylumbelliferyl choline phosphate (4 MU-CP).

The method according to the invention will be better understood by means of the examples below, which are in no way limiting in nature, in combination with the drawing in which.

EXAMPLE 1

Figure 1:
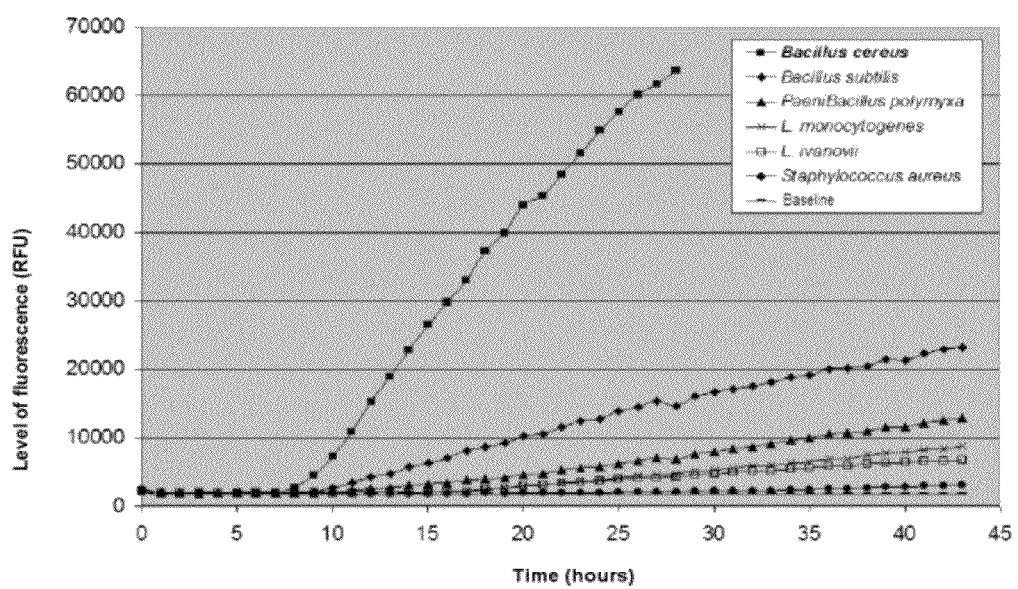
FIG. 1 illustrates kinetic measurements of the PC-PLC activity of various Gram-positive bacteria.

Study of the PC-PLC Activity of *Bacillus cereus* Compared with that Observed for other Gram-Positive Bacteria (FIG. 1 and Table 1)

Various pure strains of the *Bacillus* genus and also other Gram-positive bacteria were tested in a microplate in the presence of the medium below. A reading of the appearance of the fluorescence in each of the various wells of the microplate was then performed at different times over the course of 44 h of incubation at 37° C.

1. Medium

The medium having the following composition was used (composition in g/l), pH 7.2:

| Compounds | Concentration in g/l |
| --- | --- |
| Yeast extract | 5 |
| Sodium pyruvate | 2 |
| Magnesium glycerophosphate | 1 |
| Basic HEPES buffer | 13.8 |
| Acidic HEPES buffer | 11.92 |
| 4-Methylumbelliferyl choline phosphate[1] | 0.4 |

[1]4-Methylumbelliferyl choline phosphate (4 MU-PC), Biosynth ®, Ref. M-5528

2. Tests

The wells of the microplate are inoculated with 10 colony-forming units (CFU) of bacteria of the *Bacillus cereus* group and 1 000 CFU for the other *Bacillus* that are non *cereus* and other Gram-positive bacteria. The microplate is then incubated for 44 h at 37° C. in a microplate reader in order to evaluate the PC-PLC activity of these various strains in the form of kinetics of hydrolysis of the substrate 4 MU-CP, i.e to detect and measure the appearance of fluorescence. The detection threshold of the measuring apparatus is fixed at 30 000 RFU (relative fluorescence unit).

3. Results and Interpretation

FIG. 1 shows a significant difference between the PC-PLC activity observed in *Bacillus cereus* (positive signal from 15 hours onward) and that observed in the other Gram-positive bacteria (positive signal detectable only after 40 hours of incubation). It is not necessary to add a complex inhibiting system to the medium in order to obtain this result.

These results were confirmed for 10 strains belonging to the *Bacillus cereus* group compared with 15 other strains not belonging to the *Bacillus cereus* group. The latter results are collated in table 1.

It is therefore possible to distinguish the strains of the *Bacillus cereus* group compared with the other Gram-positive bacteria without a complex inhibitor cocktail (presence only of an anti-Gram-negative inhibitor) in a reading window of between 6 and 30 h.

TABLE 1

Level of fluorescence generated at 24 and 40 h by the
hydrolysis of 4 MU-PC by various microorganisms.

| Bacterial species | Levels of fluorescence in 24 h (RFU) | Levels of fluorescence in 40 h (RFU) |
|---|---|---|
| Bacillus cereus ATCC 7064 | >60000 | >60000 |
| Bacillus cereus ATCC 6464 | >60000 | >60000 |
| Bacillus cereus ATCC 9139 | >60000 | >60000 |
| Bacillus cereus ATCC 10876 | >60000 | >60000 |
| Bacillus cereus ATCC 33019 | >60000 | >60000 |
| Bacillus cereus NCTC 11145 | >60000 | >60000 |
| Bacillus thuringiensis 0240015 | >60000 | >60000 |
| Bacillus mycoides ATCC 6463 | >60000 | >60000 |
| Bacillus licheniformis 93.08.043 | 2000 | 2000 |
| Bacillus sphaericus 8710054 | 20000 | >60000 |
| Bacillus circulans ATCC 4513 | 10000 | 20000 |
| Bacillus subtilis ATCC 6051 | 10000 | 20000 |
| Bacillus lentus ATCC 10840 | 5000 | 10000 |
| Bacillus pumilus ATCC 7061 | 5000 | 10000 |
| PaeniBacillus polymyxa ATCC 21551 | 5000 | 10000 |
| Bacillus megaterium ATCC 14581 | 5000 | 5000 |
| L. monocytogenes ATCC 19118 | 4000 | 15000 |
| L. monocytogenes 0301902 | 5000 | 10000 |
| L. ivanovii ATCC 49954 | 2000 | 10000 |
| L. ivanovii 0002147 | 2000 | 10000 |
| S. aureus 8407603 | 2000 | 2000 |
| S. aureus 25923 | 2000 | 2000 |
| Baseline | 2000 | 2000 |

Detection threshold: 30 000 RFU. The bacteria belonging to the *Bacillus cereus* group are indicated in bold characters.

EXAMPLE 2

Figure 2:
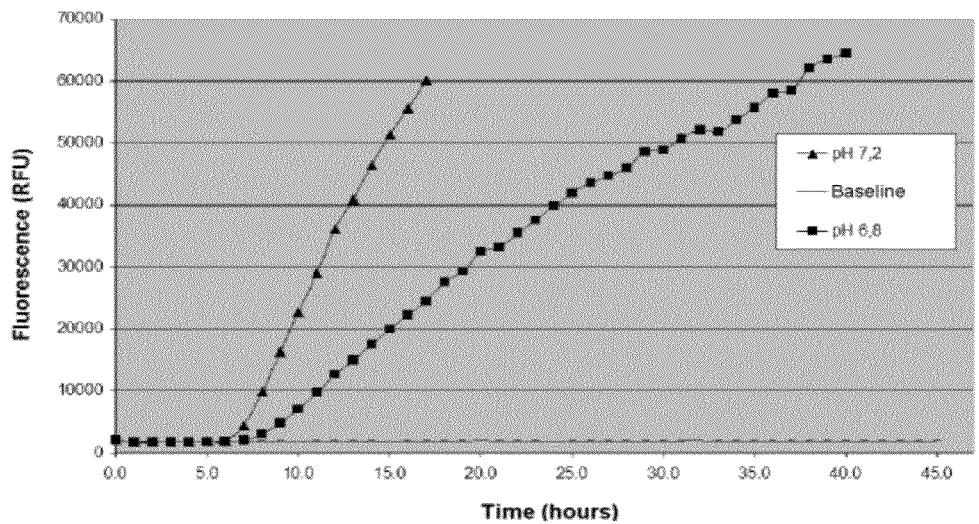
FIG. 2 illustrates the kinetic measurement of PC-PLC activity of the *Bacillus cereus* ATCC 7064 strain as a function of the pH of the medium, respectively fixed at 7.2 or 6.8.

Study of the PC-PLC Activity of *Bacillus cereus* at pH 7.2 Compared with pH 6.8 (FIG. 2)

The dynamics of the PC-PLC activity of Bacillus cereus ATCC 7064 was evaluated at pH 7.2 (medium A) compared with pH 6.8 (medium B).

1. Media
Medium A has the following composition, pH 7.2:

| Compounds | Concentration in g/l |
|---|---|
| Yeast extract | 5 |
| Sodium pyruvate | 2 |
| Magnesium glycerophosphate | 1 |
| Basic HEPES buffer | 13.8 |
| Acidic HEPES buffer | 11.92 |
| 4-Methylumbelliferyl choline phosphate | 0.4 |

Medium B has the following composition, pH 6.8:

| Compounds | Concentration in g/l |
|---|---|
| Yeast extract | 5 |
| Sodium pyruvate | 2 |
| Magnesium glycerophosphate | 1 |
| Na PIPES buffer | 16.22 |
| DiNa PIPES buffer | 17.32 |
| 4-Methylumbelliferyl choline phosphate | 0.4 |

2. Tests
Ten CFU *Bacillus cereus* ATCC 7064 were inoculated into the wells of the microplate in the presence of medium A (pH 7.2) and of medium B (pH 6.8). The microplate is then incubated for 44 h at 37° C. in a microplate reader in order to evaluate the PC-PLC activity of the *Bacillus cereus* ATCC 7064 strain at the two pHs studied.

3. Results and Interpretation
The dynamics of the PC-PLC activity of *Bacillus cereus* ATCC 7064 and the RFU signals thus obtained at pH 7.2 are greater. Indeed, the 4 MU fluorescence emission strength increases with the pH of the medium (optimum pH for emission=10).

Taking into consideration the growth and the PC-PLC activity of *Bacillus cereus*, the optimum pH of the medium is 7.2. The obtaining of greater signals therefore makes it possible to reduce the detection time, i.e by 10 h in this specific case if the detection threshold is considered at 30 000 RFU.

NB: in the case of the use of 4 MU-MIP (4-methylumbelliferyl myoinositol-1-phosphate, N-methylmorpholine salt, Biosynth®, Ref. M-5717) for distinguishing the bacteria of the *Bacillus cereus* group, this pH of 7.2 cannot be used owing to the instability of the substrate being too great. A pH of 6.8 is therefore required, leading to an increase in detection time.

EXAMPLE 3

Figure 3:
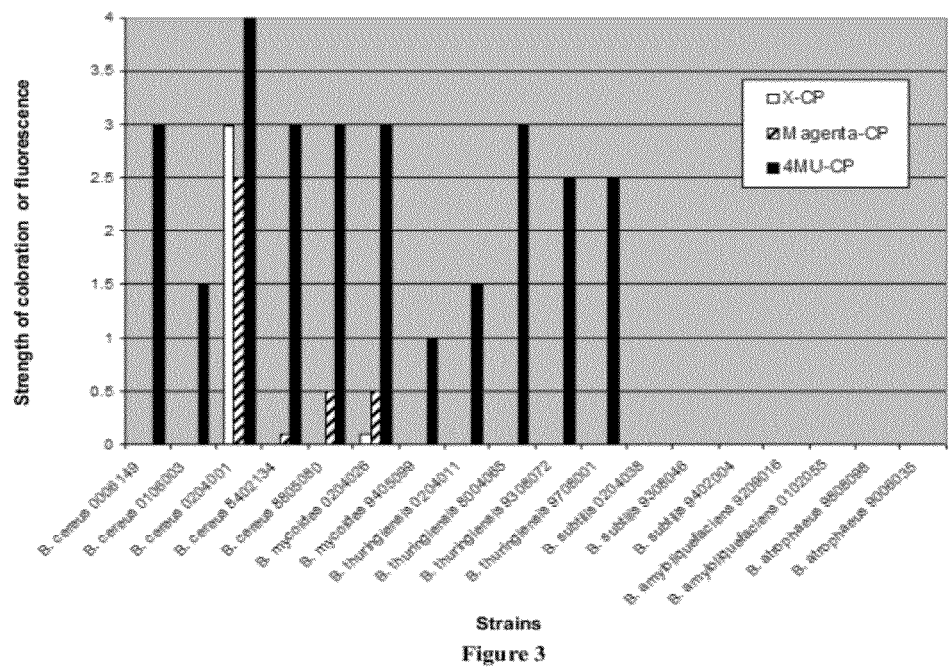
FIG. 3 illustrates the strength of coloration or of fluorescence obtained in 24 h for various strains of *Bacillus* spp as a function of the type of substrate used.

Study of the Performance Levels of Various Substrates (Chromogenic Compared with Fluorogenic) for Revealing the PC-PLC Activity of Bacteria of the *Bacillus cereus* Group Compared with *Bacillus* spp. (FIG. 3)

Various strains of the Bacillus genus were tested on 10 different media. The plates are then read after 24 h and 48 h of incubation at 37° C.

The substrates tested are 5-bromo-4-chloro-3-indoxylcholine phosphate (X-CP), which is chromogenic, 5-bromo-6-chloro-3-indoxylcholine phosphate (magenta-CP), which is chromogenic, and 4-methylumbelliferone choline phosphate (4 MU-CP), which is fluorescent.

1. Media
The medium having the following composition was used (composition in g/l):
yeast extract: 5 g/l
magnesium glycerophosphate: 1 g/l
agar: 13 g/l
LiCl: 3 g/l
MOPS: 12.6 g/l
MOPS sodium salt: 20.78 g/l This medium was distributed into 10 different bottles (T, 1, . . . , 9) which were then sterilized by means of a 15 min/121° C. autoclave cycle. The medium T serves as a growth control. Stock solutions, at 30 g/l, of 5-bromo-4-chloro-3-indoxylcholine phosphate (X-CP), 5-bromo-6-chloro-3-indoxylcholine phosphate (magenta-CP) and 4-methylumbelliferone choline phosphate (4 MU-CP) were prepared in osmosed water. Next, a volume corresponding to a final X-CP concentration of 100, 300 and 900 mg/l, respectively, was added to the molten media denoted 1, 2 and 3, respectively. The same operation is repeated for media 4, 5 and 6 and 7, 8 and 9 containing, respectively, 100, 300 and 900 mg/l of magenta-CP and 100, 300 and 900 mg/l of 4 MU-CP. These agar media were poured into Petri dishes.

2. Tests
The various *Bacillus* strains were inoculated by three-quadrant streaking using suspensions at 0.5 McF (McFarland units). The dishes were then incubated for 48 h at 37° C.

The colonies formed were examined visually after 24 and 48 h of incubation. The coloration or fluorescence (read under a UV lamp at 366 nm) of these colonies and also the strengths were noted.

3. Results

The coloration and fluorescence strengths are read on a relative scale ranging from 0 (no coloration/fluorescence) to 4 (very strong coloration/fluorescence). The results are illustrated in FIG. 3 (expression of the PC-PLC activity after 24 h of incubation on various Bacillus species). The absence of a bar indicates that the coloration or fluorescence strength measured is not significantly different than the background noise, it is therefore a negative result.

4. Interpretation

The use of the fluorogenic PC-PLC substrate 4 MU-CP, unlike the chromogenic substrates (X-CP and magenta-CP) makes it possible to detect and distinguish bacteria of the *Bacillus cereus* group compared with the *Bacillus subtilis* with high detection sensitivity and specificity (100%), in particular after 24 h of incubation at 37° C. and on all the strains tested.

The invention claimed is:

1. A method for identifying bacteria of the *Bacillus cereus* group, comprising the following steps:

(a) providing a sample containing bacteria of the *Bacillus cereus* group and Gram-positive bacteria other than those belonging to the *Bacillus cereus* group, a reaction medium comprising at least one fluorescent phosphatidylcholine phospholipase C (PC-PLC) substrate and an inhibitor of Gram-negative bacteria, wherein said reaction medium does not contain an inhibitor of Gram-positive bacteria, and wherein the pH of the reaction medium is between 6.8 and 8.0;

(b) inoculating the reaction medium with said sample;

(c) incubating the inoculated reaction medium; and (d) identifying the bacteria of the *Bacillus cereus* group by detecting hydrolysis of the PC-PLC substrate, wherein detection of the hydrolyzed PC-PLC substrate at between 6 and 30 hours results in identification of said bacteria of the *Bacillus cereus* group, and wherein said method allows for detection of bacteria of the *Bacillus cereus* group before the hydrolysis of the PC-PLC substrate by Gram-positive bacteria other than those belonging to the *Bacillus cereus* group.

2. The method as claimed in claim 1, wherein the reaction medium is in liquid, gel or solid form.

3. The method as claimed in claim 1, wherein the reaction medium is a culture medium.

4. The method as claimed in claim 1, further comprising a prior step of enrichment of the sample.

5. The method as claimed in claim 1, wherein the medium also comprises at least one second substrate, which is chromogenic or fluorescent.

6. The method as claimed in claim 5, wherein the second substrate is a phosphatidylinostol-specific phospholipase C (PI-PLC) substrate which makes it possible to distinguish *Bacillus anthracis* from *Bacillus cereus, Bacillus thuringiensis, Bacillus weihenstephanensis, Bacillus mycoides* and *Bacillus pseudomycoides.*

7. The method as claimed in claim 1, wherein the bacteria of the *Bacillus cereus* group are counted.

8. The method as claimed in claim 1, wherein the method is carried out in a container and the container is selected from the group consisting of microplates, microwells, microtubes, capillaries or multiwell cards.

9. The method as claimed in claim 1, wherein the fluorescent PC-PLC substrate is 4-methylumbelliferyl choline phosphate (4 MU-CP).

10. The method as claimed in claim 1, wherein the bacteria of the *Bacillus cereus* group are chosen from selected from the group consisting of *Bacillus cereus, Bacillus anthracis, Bacillus thuringiensis, Bacillus mycoides, Bacillus pseudomycoides and Bacillus weihenstephanensis*, and the other bacteria are chosen from selected from the group consisting of *Listeria monocytogenes, Listeria ivanovii, Staphylococcus* or the other species of the genus *Bacillus spp.*, such as *Bacillus subtilis, Bacillus sphaericus, Bacillus circulans, Bacillus lentus, Bacillus pumilus, Bacillus megaterium* and *Paenibacillus polymyxa.*

* * * * *